United States Patent
Broom et al.

(10) Patent No.: US 9,216,240 B2
(45) Date of Patent: Dec. 22, 2015

(54) DIFFERENTIAL LOADING OF DRUG-ELUTING MEDICAL DEVICES

(75) Inventors: Daniel Broom, Branford, CT (US); Joshua Stopek, Guilford, CT (US); Amin Elachchabi, Hamden, CT (US)

(73) Assignee: Covidien LP, Mansfield, MA (US)

( * ) Notice: Subject to any disclaimer, the term of this patent is extended or adjusted under 35 U.S.C. 154(b) by 564 days.

(21) Appl. No.: 12/987,259

(22) Filed: Jan. 10, 2011

(65) Prior Publication Data

US 2011/0189270 A1 Aug. 4, 2011

Related U.S. Application Data

(60) Provisional application No. 61/301,007, filed on Feb. 3, 2010.

(51) Int. Cl.
*A61K 9/48* (2006.01)
*A61L 31/16* (2006.01)
*A61L 15/44* (2006.01)
*A61L 27/54* (2006.01)

(52) U.S. Cl.
CPC ............... *A61L 31/16* (2013.01); *A61L 15/44* (2013.01); *A61L 27/54* (2013.01); *A61L 2300/402* (2013.01); *A61L 2300/45* (2013.01); *A61L 2300/602* (2013.01)

(58) Field of Classification Search
CPC ............ C12N 2535/10; C12N 5/0068; C12N 2533/56; A61L 27/38; A61L 27/60; A61L 15/44; A61L 27/54; A61L 2300/602; A61L 2300/402; A61L 2300/45; A61L 31/16
See application file for complete search history.

(56) References Cited

U.S. PATENT DOCUMENTS

| | | | |
|---|---|---|---|
| 6,326,020 B1 * | 12/2001 | Kohane et al. | 424/426 |
| 6,596,296 B1 | 7/2003 | Nelson et al. | |
| 7,517,362 B2 | 4/2009 | Shanley et al. | |
| 2003/0175410 A1 * | 9/2003 | Campbell et al. | 427/2.24 |
| 2004/0019360 A1 | 1/2004 | Farnsworth et al. | |
| 2004/0172048 A1 | 9/2004 | Browning | |
| 2004/0253185 A1 | 12/2004 | Herweck et al. | |
| 2005/0010170 A1 | 1/2005 | Shanley et al. | |
| 2005/0106211 A1 * | 5/2005 | Nelson et al. | 424/423 |
| 2006/0045903 A1 | 3/2006 | Kadiyala et al. | |
| 2006/0246109 A1 | 11/2006 | Hossainy et al. | |
| 2007/0077272 A1 | 4/2007 | Li et al. | |
| 2007/0123915 A1 | 5/2007 | Kammerer et al. | |
| 2009/0226506 A1 | 9/2009 | Masters et al. | |
| 2010/0330181 A1 * | 12/2010 | Castiglione-Dodd et al. | 424/484 |

OTHER PUBLICATIONS

European Search Report, Application No. EP 11 25 0117 dated Jun. 6, 2014.

* cited by examiner

*Primary Examiner* — Suzanne Ziska

(57) ABSTRACT

A medical device includes a substrate having at least one surface. The surface has a central portion and a peripheral portion. At least one bioactive agent is disposed over at least a portion of the surface. The medical device having a concentration gradient of the at least one bioactive between the central and peripheral portions.

20 Claims, 4 Drawing Sheets

DIFFERENTIAL LOADING OF DRUG-ELUTING MEDICAL DEVICES

CROSS-REFERENCE TO RELATED APPLICATIONS

This application claims the benefit of and priority to U.S. Provisional Patent Application No. 61/301,007, filed Feb. 3, 2010, the entire disclosure of which is incorporated by reference herein.

TECHNICAL FIELD

The present disclosure relates to drug delivering medical devices. More particularly, the present disclosure relates to medical and/or surgical implants having a drug dose concentration gradient imparted thereto, and methods of forming and using the same, for tailored localized drug delivery to tissue within a surgical site.

BACKGROUND

Surgical implants, such as drug eluting devices, are known to serve as vehicles for the delivery of drugs or other therapeutics. Typically, devices, such as stents, are coated with a biologically active agent to provide treatment to an implant site. It is generally desirable that an effective therapeutic amount of a selected drug be released from the device at a certain rate for an extended period of time. The release of the drug from the coating medium may be dependent upon the nature of the coating material and the drug that is incorporated therein, with drug release occurring by diffusion through the coating material or with degradation of the coating material.

Moreover, implants, such as meshes, are generally customized and cut to a desired size based on anatomical need. However, any cutting or trimming of a drug-eluting implant may affect the drug payload of the device.

Thus, it would be advantageous to provide medical devices including a controllable drug release concentration gradient. It would also be advantageous to provide a device which may be trimmed or cut without affecting the total drug payload of the device.

SUMMARY

A medical device in accordance with the present disclosure includes a central portion and a peripheral portion having a concentration gradient of a first bioactive agent between the central and peripheral portions. In embodiments, the gradient increases in concentration from the central portion to the peripheral portion. In other embodiments, the gradient increases in concentration from the peripheral portion to the central portion of the medical device.

According to one embodiment of the present disclosure, a medical device includes a substrate having at least one surface. The surface has a central portion and a peripheral portion. A first bioactive agent is disposed over at least a portion of the surface. A higher concentration of the first bioactive agent is positioned on the central portion of the substrate and a lower concentration of the first bioactive agent extends outwardly from the central portion to the peripheral portion of the substrate.

The bioactive agent may extend through the peripheral portion of the surface of the substrate. In other embodiments, the substrate includes an intermediate portion positioned between the central portion and the peripheral portion, in which the lower concentration of the bioactive agent is disposed.

The bioactive agent may be disposed on the surface of the substrate as a substantially continuous concentration gradient, or alternatively, as a discontinuous concentration gradient. In embodiments, the intermediate portion includes successive sections separately extending away from the central portion, wherein the bioactive agent decreases in concentration through each successive section towards the peripheral portion of the substrate. The successive sections, in embodiments, may be annular rings which are concentric to the central portion of the substrate. In other embodiments, the successive sections may be bands longitudinally aligned with the central portion of the substrate.

The bioactive agent may be disposed, for example, within the materials which form the medical device, or the bioactive agents may be disposed in a coating composition, polymeric film, foam, or encapsulated within a polymeric material in a flowable state. In embodiments the intermediate portion of the substrate includes a plurality of polymeric capsules containing the bioactive agent in a flowable state.

In some embodiments, the substrate may include a concentration gradient of the bioactive agent in a height dimension of the substrate. For example, the bioactive agent may be disposed within pores of the substrate thereby creating a concentration gradient in the height dimension.

In alternate embodiments, the substrate may include a lower concentration of a first bioactive agent on a central portion of the substrate, while a higher concentration of the second bioactive agent extends outwardly from the central portion towards the peripheral portion of the substrate. The first bioactive agent may be different than the second bioactive agent. Further, the lower concentration may be more therapeutically effective compared to the higher concentration.

The first or second bioactive agents may comprise capsaicin, bupivacaine or bupivacaine hydrochloride.

The medical device may also include markings on the substrate for visualization of the bioactive agent.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
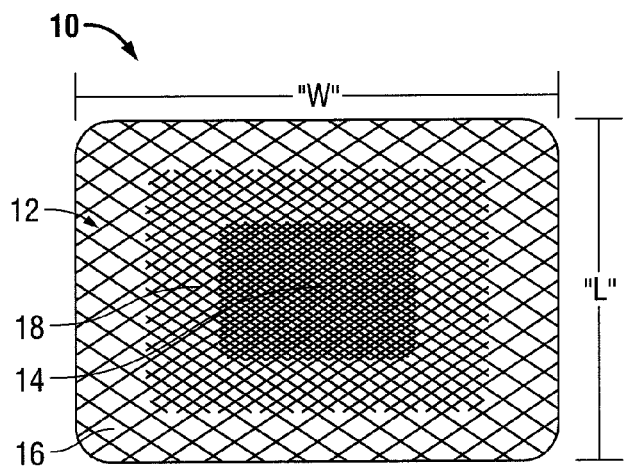
FIG. 1 schematically shows a medical device having a substantially continuous gradient of a bioactive agent over a surface of the medical device in accordance with an embodiment of the present disclosure.

Medical devices in accordance with the present disclosure include a substrate upon, or within, which desired bioactive agent(s) may be applied to, or otherwise loaded therein or therethrough, for therapeutic treatment of tissue. The medical device may be any surgical implant, such as meshes, (tissue) scaffolds, grafts, stents, sutures, patches, slings, buttresses, pledgets, soft tissue repair devices, and in general, any mechanical, electrical or digital implants. Some other non-limiting examples include soft tissue repair devices, surgical prostheses, and artificial organs; or topically applied medical products, such as wound dressings, coverings, tapes, gauzes, and the like, that can be used in medical/surgical procedures.

In embodiments, the medical device may include pores or openings on at least a portion of a surface thereof, within which the bioactive agent(s) may be disposed. The pores may be present as a surface characteristic or a bulk material property, which partially or completely penetrates the medical device, and may be uniformly distributed across portions thereof. The medical device may have an open-cell structure, where the pores are connected to each other, forming an interconnected network. Conversely, the medical device may be closed cell, where the pores are not interconnected. Those skilled in the art reading the present disclosure may envision other pore distribution patterns and configurations. The pores may be created using any method within the purview of those skilled in the art including, but not limited to, lyophilization or freeze-drying, sintering, leaching of salt, and sugar or starch crystals. Alternatively, openings may be formed in filamentous medical devices, such as sutures and meshes, via the spaces formed between the filaments.

In some embodiments, medical devices of the present disclosure possess at least one bioactive agent which is disposed on at least a portion of the medical device. In embodiments the bioactive agent may be in the form of a single coating, or multiple coatings. The coatings of course may be continuous or discontinuous. Thus, the bioactive agent may be coated on, or impregnated in, a medical device of the present disclosure to provide specific biological or therapeutic properties thereto. The term "bioactive agent," as used herein, is used in its broadest sense and includes any substance or mixture of substances that have clinical use. Consequently, bioactive agents may or may not have pharmacological activity per se, e.g., a dye. A bioactive agent could be any agent which provides a therapeutic or prophylactic effect; a compound which may be used as a diagnostic aid; a compound that affects or participates in tissue growth, cell growth and/or cell differentiation; a compound that may be able to invoke or prevent a biological action such as an immune response; or a compound that could play any other role in one or more biological processes. Moreover, any agent which may enhance tissue repair or tissue integration, limit the risk of sepsis, modulate the mechanical properties of the medical device, and/or deliver pharmaceutical agents may be incorporated to the device. A single bioactive agent may be utilized or, in alternate embodiments, a variety of bioactive agents may be incorporated into the medical devices of the present disclosure.

In embodiments, a first bioactive agent may be disposed on at least a portion of the medical device in a manner which creates a concentration gradient from the central portion of the medical device extending outwardly towards the peripheral portion of the medical device. It is envisioned that any number of additional bioactive agents may also be disposed on the medical devices. It is further envisioned that the additional bioactive agents may be positioned in any concentration and on any portion of the medical devices.

Examples of classes of bioactive agents, which may be utilized in accordance with the present disclosure include, for example, anti-adhesives, antimicrobials, analgesics, antipyretics, anesthetics (e.g. local, regional, and systemic), anti-epileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, phosphoryl cholines, lipopolysaccharides, polysaccharides, platelet activating drugs, clotting factors, and enzymes. It is also intended that combinations of bioactive agents may be used.

Other bioactive agents, which may be included as a bioactive agent include: anti-fertility agents; parasympathomimetic agents; psychotherapeutic agents; tranquilizers; decongestants; sedative hypnotics; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics; estrogens; antibacterials; antibiotics; anti-fungals; anti-virals; anticoagulants; anticonvulsants; antidepressants; and immunological agents.

Other examples of suitable bioactive agents, which may be included in the medical device include, for example, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (e.g., IL-2, IL-3, IL-4, IL-6); interferons (e.g., $\beta$-IFN, $\alpha$-IFN and $\gamma$-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-β; protein inhibitors; protein antagonists; protein agonists; nucleic acids such as antisense molecules, DNA, RNA, and RNAi; oligonucleotides; polynucleotides; and ribozymes.

In embodiments, the bioactive agent may include at least one of the following drugs, including combinations and alternative forms of the drugs such as alternative salt forms, free acid form, free base forms, pro-drugs and hydrates. Specific agents within these classes are within the purview of those skilled in the art and are dependent upon such factors as, for example, the type of device in which it is utilized and the tissue being treated. Thus, for example, local anesthetics such as bupivacaine (which may be sold under Marcain™, Marcaine™, Sensorcaine™ and Vivacaine™ all by Astra-Zeneca), levobupivacaine (sold under Chirocaine™ by Astra-Zeneca), ropivacaine, lidocaine, and the like, may be used alone or in combination for treatment of pain or for anesthetic purposes. In embodiments, antimicrobial agents such as triclosan, also known as 2,4,4'-trichloro-2'-hydroxydiphenyl ether; chlorhexidine and its salts, including chlorhexidine acetate, chlorhexidine gluconate, chlorhexidine hydrochloride, and chlorhexidine sulfate; silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine; polymyxin; tetracycline; aminoglycosides such as tobramycin and gentamicin; rifampicin; bacitracin; neomycin; chloramphenicol; miconazole; quinolones such as oxolinic acid, norfloxacin, nalidixic acid, pefloxacin, enoxacin and ciprofloxacin; penicillins such as oxacillin and pipracil; nonoxynol 9; fusidic acid; and cephalosporins; may also be used alone or in combination for the treatment of microbial growth. In addition, antimicrobial proteins and peptides, such as lactoferrin and lactoferricin B, and antimicrobial polysaccharides, such as fucans and derivatives thereof, may be included as a bioactive agent in the present disclosure to kill or prevent microbial growth. And anti-adhesive agents may be used to prevent adhesions from forming between the coated medical device and the surrounding tissues. Some examples of these agents include, but are not limited to, poly(vinyl pyrrolidone), carboxymethyl cellulose, hyaluronic acid, alginate, collagen, polyethylene glycol, polyethylene oxide, polypropylene glycol, poly vinyl alcohols, poly acrylic acid, styrene sulfonic acid, polyhydroxyethylmethylacrylate, (pHEMA) and phospholipid vinyls; acrylic polymers such as sodium polyacrylate, polyethylacrylate, and polyacrylamide, polypropylene oxide, phosphorylcholine functional acrylates and methacrylates; homopolymers and combinations thereof.

The bioactive agent(s) may be incorporated into or onto the medical device by coating a surface of the device, or portion thereof, in a variety of ways. For example, the bioactive agents may be applied via polymer coating, dry coating, freeze drying, and ionically, covalently, or affinity binding to a surface thereof. A coating may be applied to the medical device utilizing any suitable method known to those skilled in the art. Some examples include, but are not limited to, spraying, dipping, layering, casting, calendering, etc.

In some embodiments, one or more bioactive agents may be applied to a medical device as a composition or coating dispersed in a suitable biocompatible solvent. Suitable solvents for particular bioactive agents are within the purview of those skilled in the art. In one example, a bioactive agent such as bupivacaine may be combined with a chlorinated solvent such as methylene chloride. In other embodiments, one or more bioactive agents may be combined with a biodegradable polymer which releases the bioactive agent(s) during degradation of the polymer. The bioactive agents may be freely admixed with the polymeric material or may be tethered to the polymer through any suitable chemical bonds. In embodiments, the therapeutic agent may include at least one of the following drugs, including combinations and alternative forms of the drugs such as alternative salt forms, free acid form, free base forms, pro-drugs and hydrates: In yet other embodiments, one or more bioactive agents may be encapsulated within a polymeric material in a flowable, or non-solid, state. The polymeric material may be rapidly bioerodible, or otherwise penetrable, to provide quick release of the bioactive agent(s) into the surrounding tissue.

The term "biodegradable" as used herein is defined to include both bioabsorbable and bioresorbable materials. By biodegradable, it is meant that the material decomposes, or loses structural integrity under body conditions (e.g., enzymatic degradation or hydrolysis) or is broken down (physically or chemically) under physiologic conditions in the body such that the degradation products are excretable or absorbable by the body. It should be understood that such materials include natural, synthetic, bioabsorbable, and/or non-absorbable materials, as well as combinations thereof.

Representative natural biodegradable polymers which may be used with the bioactive agent include: poly(amino acids) including proteins such as collagen (I, II and III), elastin, fibrin, fibrinogen, silk, and albumin; peptides including sequences for laminin and fibronectin (RGD); polysaccharides such as hyaluronic acid (HA), dextran, alginate, chitin, chitosan, cellulose, fucans, glycosaminoglycans, and chemical derivatives thereof (substitutions and/or additions of chemical groups, for example, alkyl, alkylene, hydroxylations, oxidations, and other modifications routinely made by those skilled in the art); gut; and copolymers and blends thereof, alone or in combination with synthetic polymers. Collagen as used herein includes natural collagen such as animal derived collagen, gelatinized collagen, or synthetic collagen such as human or bacterial recombinant collagen.

Synthetically modified natural polymers include cellulose derivatives, such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt.

Representative synthetic biodegradable polymers include polyhydroxy acids prepared from lactone monomers, such as glycolide, lactide, caprolactone, ε-caprolactone, valerolactone, and δ-valerolactone, as well as carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: poly(lactic acid); poly(glycolic acid); poly(trimethylene carbonate); poly(dioxanone); poly(hydroxybutyric acid); poly(hydroxyvaleric acid); poly(lactide-co-(ε-caprolactone-)); poly(glycolide-co-(ε-caprolactone)); poly(lactic-co-glycolic acid); polycarbonates; poly(pseudo amino acids); poly(amino acids); poly(hydroxyalkanoate)s; polyalkylene oxalates; polyoxaesters; polyanhydrides; polyortho esters; and copolymers, block copolymers, homopolymers, blends, and combinations thereof.

Other non-limiting examples of biodegradable materials include: aliphatic polyesters; polyethylene glycols; glycerols; copoly (ether-esters); and copolymers, block copolymers, homopolymers, blends, and combinations thereof.

Rapidly bioerodible polymers, such as poly(lactide-co-glycolide)s, polyanhydrides, and polyorthoesters, which have carboxylic groups exposed on the external surface as the surface of the polymer erodes, may also be used.

Where the coating includes a biodegradable polymeric material, the bioactive agent may be released into the body within a period of time ranging from about 1 second to about 21 days following implantation. In one embodiment, the agent may be released within about 1 minute to about 14 days following implantation.

The rate of release of a bioactive agent from the coating may be controlled by various methods. Some examples include, but are not limited to, the depth of the bioactive agent from the surface of the coating; the size of the bioactive agent; the hydrophilicity or lipophilicity of the bioactive agent; the molecular structure of the bioactive agent; the pH and/or the ionization of the agent/coating; and the strength of physical and physical-chemical interaction between the bioactive agent, the coating composition, and/or the medical device material. By properly controlling some of these factors, a controlled release of a bioactive agent from the medical device of the present disclosure can be achieved.

Embodiments of the present disclosure will now be described below while referencing the accompanying figures. The accompanying figures are merely examples and are not intended to limit the scope of the present disclosure.

Referring now to the drawings wherein like components are designated by like reference numerals throughout the several views, FIG. 1 illustrates a medical device in the form of a mesh 10, according to an embodiment of the present disclosure. Mesh 10 may be in the form of a plurality of fibers (not shown) defining a longitudinal length "L" and a lateral, transverse width "W". Mesh 10 includes a bioactive agent 12 coated over the surface of the mesh 10. Central portion 14 of mesh 10 includes the highest concentration of bioactive agent 12, which gradually decreases, or tapers off, to the peripheral portion 16 of mesh 10 through intermediate portion 18. Thus, the bioactive agent 12 is disposed on mesh 10 in a substantially continuous gradient from a higher concentration at the central portion 14 of the mesh 10, to a lower concentration at the peripheral portion 16 of the mesh 10.

In certain embodiments, the ratio of the bioactive agent concentration from the central portion 14 to the peripheral portion 16 of mesh 10 is at least 1.1:1 by percent weight. In embodiments, the ratio may be from about 20:1 to about 2:1, and in some embodiments, from about 10:1 to about 5:1.

The mesh of the present disclosure allows for the specific delivery of the bioactive agent while still providing the surgeon with the ability to customize the size of the mesh based on the anatomical need of the patient by maintaining the majority of the bioactive agent dosing in the central portion of the device. The surgeon may still trim the edges or peripheral portions of the mesh without affecting the total drug payload. Moreover, because the majority of the bioactive agent dosing is in the central portion of the device, a variety of different meshes can be manufactured using the same drug loading specification.

Figure 2:
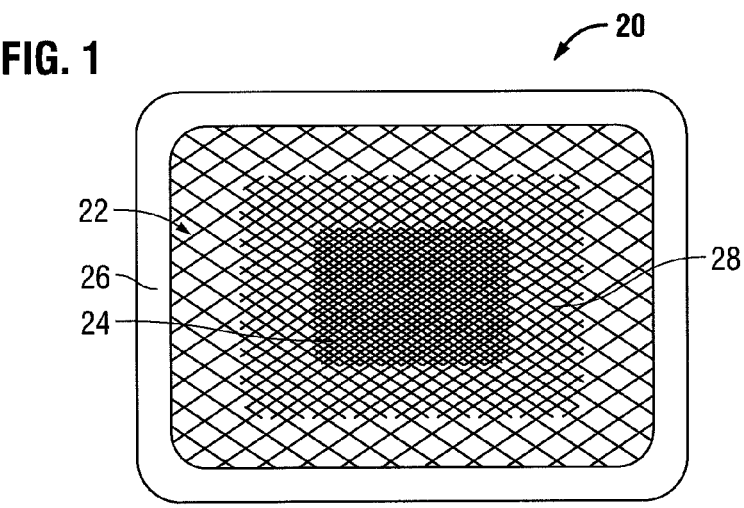
FIG. 2 schematically shows a medical device having a substantially continuous gradient of a bioactive agent over a portion of a surface of the medical device in accordance with another embodiment of the present disclosure.

Alternatively, a select portion of a surface of a mesh may be drug-loaded thereby providing areas of the mesh without drug-loading (bioactive agents) as illustrated, for example, in FIG. 2. Mesh 20 includes central portion 24, intermediate portion 28, and peripheral portion 26. The central portion 24 has a higher concentration of bioactive agent 22 than the intermediate portion 28, and the peripheral portion 26 is not coated with any bioactive agent 22. This configuration would potentially allow the surgeon to cut the mesh 20 without affecting any of the drug payload.

Accordingly, the portion of the mesh to be drug-loaded and the surrounding low dose or uncoated area may vary in size or pattern depending upon a number of factors, such as the amount of drug to be loaded, the size of the mesh, and the amount of mesh which may be removed prior to implantation by the surgeon, for example.

Figure 3:
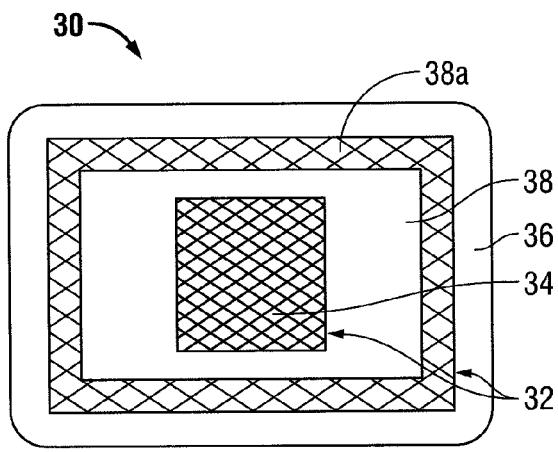
FIG. 3 schematically shows a medical device having a discontinuous gradient of a bioactive agent in accordance with one embodiment of the present disclosure.
Figure 4:
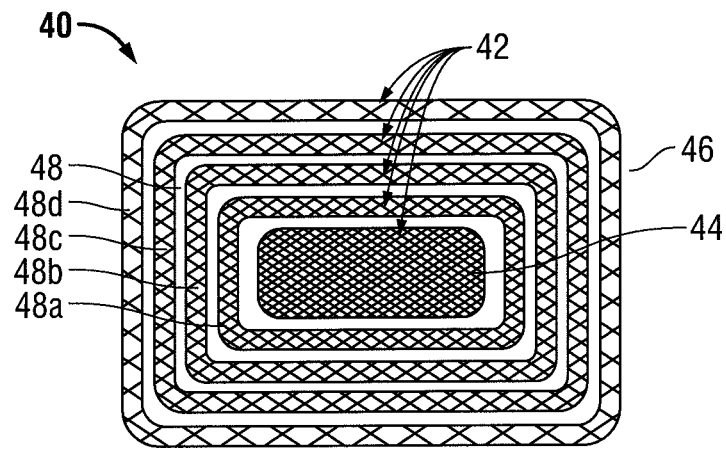
FIG. 4 schematically shows a medical device having a discontinuous gradient of a bioactive agent in accordance with another embodiment of the present disclosure.

The bioactive agent may also be disposed in a radially, discontinuous gradient from a higher concentration to a lower concentration as illustrated in FIGS. 3 and 4. As shown in FIG. 3, bioactive agent 32 is distributed on mesh 30 to form a concentration gradient which includes a higher concentration about the central portion 34 of mesh 30 and a lower concentration in a predefined section 38a of intermediate portion 38 extending away from the central portion 34. The central portion 34 and intermediate portion 38 are divided by a portion of mesh 30 which does not contain a bioactive agent. The bioactive agent 32 is concentrated in the central portion 34 and has a decreased concentration in the section 38a of intermediate portion 38, such that the gradient distribution is decreased stepwise. For example, central portion 34 may include 150 mg of bupivacaine, while section 38a may be formulated to include 75 mg of bupivacaine.

In another non-limiting example, the area of central portion 34 and section 38a may both equal 25 cm$^2$. Central portion 34 may include 500 mg of a bioactive agent, while section 38a includes 350 mg of a bioactive agent. Adjusted for surface area, the payload for central portion 34 is 500 mg/25 cm$^2$ or 20 mg/cm$^2$. Similarly, the payload for section 38a is 350 mg/25 cm$^2$ or 14 mg/cm$^2$. It should be understood that these payloads are non-limiting and exemplary.

Similar to FIG. 3, FIG. 4 illustrates a radially extending, discontinuous concentration gradient decreasing from the central portion 44 through successive sections 48a, 48b, 48c, and 48d of intermediate portion 48 toward the peripheral portion 46 of mesh 40. In the current embodiments, sections 38a as well as 48a, 48b, 48c, and 48d of intermediate portions 38 and 48 are annular rings extending around central portions 34 and 44. It should be understood that the bioactive agent may be incorporated in the mesh in discontinuous rings and/or section of the mesh, and further that portions of the mesh may or may not include at least one bioactive agent. It should further be understood that the sections which include at least one bioactive agent can have any configuration extending through the intermediate portion as contemplated by those skilled in the art.

Each bioactive agent containing portion (i.e., the central portion and the intermediate portion) may include different types of bioactive agents in different combinations and amounts. For example, in some embodiments, the central portion 44 and successive sections 48a, 48b, 48c, and 48d of intermediate portion 48 of FIG. 4 may uniformly include decreasing amounts of a single or multiple bioactive agents. In other embodiments, the central portion 44 may include a high concentration of one or more bioactive agents that decreases through a select number of sections of intermediate portion 48 (e.g., through section 48c) and one or more other bioactive agents that decreases in concentration through only the intermediate portion 48 (e.g., from sections 48a through 48d). In yet other embodiments, the bioactive agents may be disposed only through segments of the bioactive agent containing portions (e.g., one bioactive agent may be disposed on one half of the mesh and a second bioactive agent is disposed on the other half of the mesh). It should be understood that various combinations of bioactive agents and placement thereof on the medical device may be utilized in accordance with the present disclosure.

Figure 5:
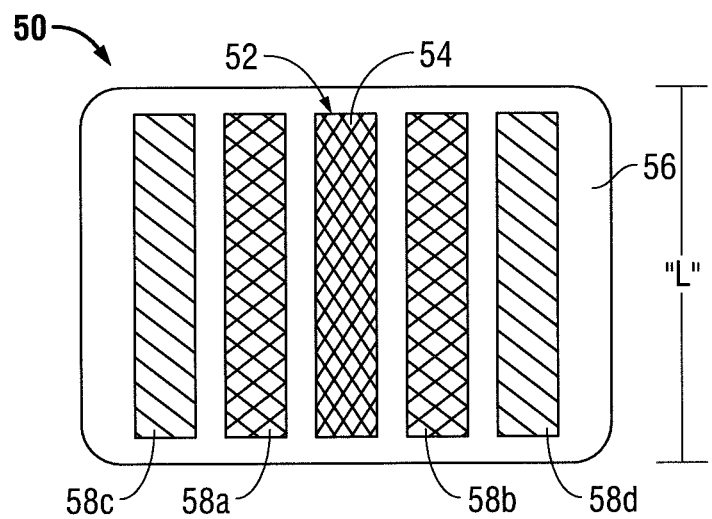
FIG. 5 schematically shows a medical device having a discontinuous gradient of a bioactive agent in accordance with yet another embodiment of the present disclosure.

Moreover, any portion of the mesh may include any number, size and shape of gradient coatings. As illustrated in FIG. 5, the bioactive agent 52 may be applied in any shape to the mesh 50 so long as the concentration gradient of the bioactive agent tapers from the central portion 54 towards the peripheral portion 56 of the mesh 50. Mesh 50 includes a central portion 54 having the highest concentration of bioactive agent 52 and successive section 58a, 58b, 58c, and 58d in the form of bands which extend longitudinally along the length "L" of the mesh 50 and laterally outward from the central portion 54. Each section 58a, 58b, 58c, and 58d include successively lower concentrations of bioactive agent 52 as they extend toward peripheral portion 56.

The bioactive agent may be applied to the mesh as a coating composition, film, or foam as described above. For example, in embodiments, a composition including a bioactive agent and a suitable solvent may be sprayed onto the mesh in successive coatings to form the concentration gradient along a portion of a surface thereof. In other embodiments, microspheres of a bioactive agent may be embedded within a polymeric material and cured to form a film which may be applied to the mesh. In yet other embodiments, a bioactive agent may be contained within or coated thereon a lyophilized foam which may be applied to the mesh. In yet alternate embodiments, the bioactive agent may be contained within the fibers or filaments of the mesh, for example, by compounding a suitable bioactive agent within the polymer resin.

Figure 6:
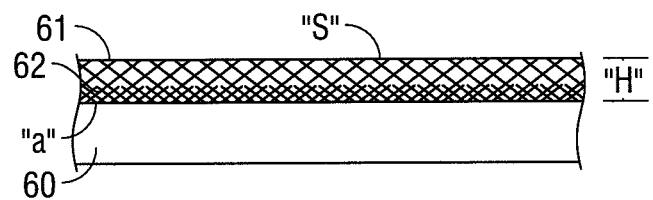
FIG. 6 schematically shows a medical device having a gradient of a bioactive agent in a height dimension in accordance with an embodiment of the present disclosure.

As illustrated in FIG. 6, the mesh may also include a bioactive agent 62 having a concentration gradient in the height dimension "H" of the mesh 60. As illustrated, a film 61 containing bioactive agent 62 is formed over mesh 60. The attached surface "a" of the film 61 contains a high concentration of bioactive agent 62 which decreases towards free surface "s". In other embodiments, the free surface of film 61 may have a high concentration of bioactive agent 62 which decreases toward the attached surface "a." In yet other embodiments, the film 61 may have a high concentration in the center which decreases towards both the free surface "s" and the attached surface "a." Alternatively, the pores or openings formed in the medical device itself may be utilized for deposition of the bioactive agent thus creating a concentration gradient in the height dimension.

Figure 7:
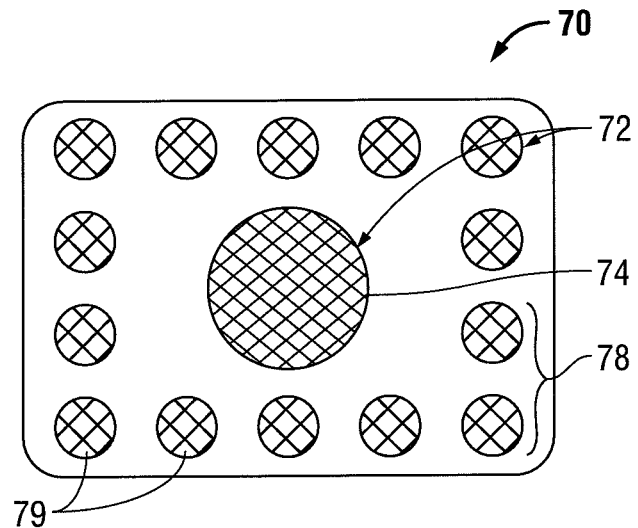
FIG. 7 schematically shows a medical device having a discontinuous gradient of a bioactive agent in accordance with yet another embodiment of the present disclosure.

Referring now to FIG. 7, another form of differential drug loading may be achieved in which the bioactive agent 72 may be encapsulated within a polymeric material in a flowable, or non-solid, state and applied to the mesh 70. Mesh 70 includes a central portion 74 including a dried coating, film, or foam of bioactive agent disposed thereon as described above. The intermediate portion 78 of mesh 70 is a discontinuous belt of polymeric capsules 79 containing bioactive agent 72. The polymeric capsules 79 may be a pocket or patch of polymeric material containing a reservoir of bioactive agent in solution, gel, particulate, or foam forms. The polymeric pocket or patch may be composed of a rapidly bioerodible polymer for quick degradation and release of the bioactive agent, or may be breakable via an external force for release of the bioactive agent.

In embodiments, the polymeric capsules 79 may aid the surgeon in visualization of the mesh, as well as placement of fasteners, such as tacks or sutures, to fixate the mesh. In embodiments, the polymeric capsules 79 are penetrated with a surgical fastener, thereby rapidly releasing the bioactive agent onto the surrounding tissue providing immediate therapeutic relief. For example, the polymeric capsules 79 may be filled with anesthetics to aid in controlling pain upon mesh fixation. The anesthetics may be used in combination with antiseptics or antibiotics to aid in preventing/treating post-attachment infection, with anti-inflammatories to aid in preventing/treating post-attachment swelling, or with other medicaments as is within the purview of those skilled in the art. Thus, the polymeric capsules 79 will allow the surgeon to more easily orientate the mesh within the surgical site, properly fasten the mesh against the tissue, and decrease the pain or discomfort associated with fastening the mesh by providing immediate medication to the site.

The portions of the mesh which contain or are coated with bioactive agent(s) may be clearly marked on the mesh itself for visualization by the surgeon. These markings may be applied by utilizing ink that may be visualized under visible, infrared, ultraviolet, and/or by other wavelengths of light.

Figure 8:
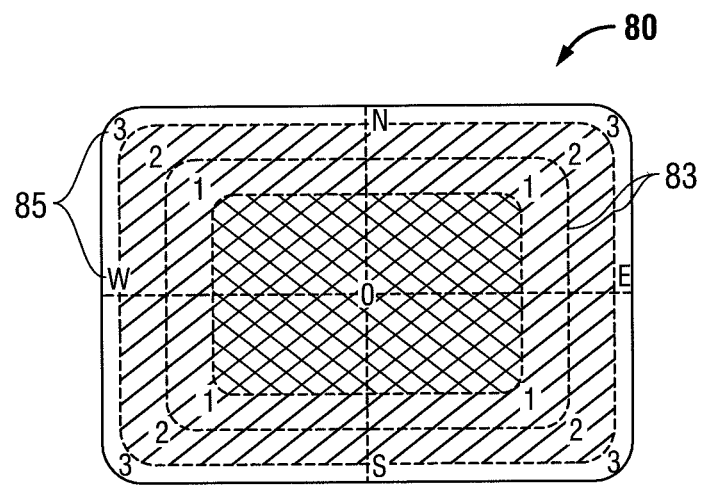
FIG. 8 schematically shows a medical device having a substantially continuous gradient of a bioactive agent as well as orientation lines and markings in accordance with an embodiment of the present disclosure.
Figure 9:
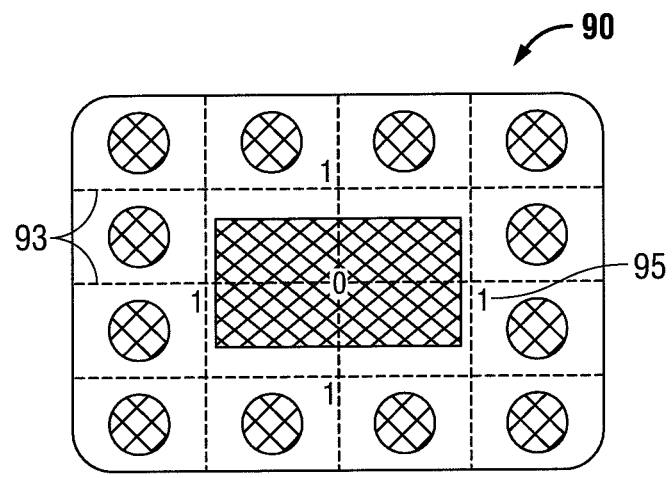
FIG. 9 schematically shows a medical device having a discontinuous gradient of a bioactive agent as well as orientation lines and markings in accordance with another embodiment of the present disclosure.

The meshes may also be marked with orientation lines, making it easy for the surgeon to orient the mesh relative to both the center of the mesh and the location of drug loading. The orientation lines may be solid or dotted/dashed lines, curves, or other written indicia. These markings may be linear or concentric in nature and can be identified by distance measurements (e.g., ⅛ inch, cm, or mm), location measurements (e.g., north, east, south west), and/or positioning markings (e.g., arrows, text). Some illustrate examples of meshes 80, 90 with orientation lines 83, 93 and markings 85, 95 are illustrated in FIGS. 8 and 9, respectively.

Figure 10:
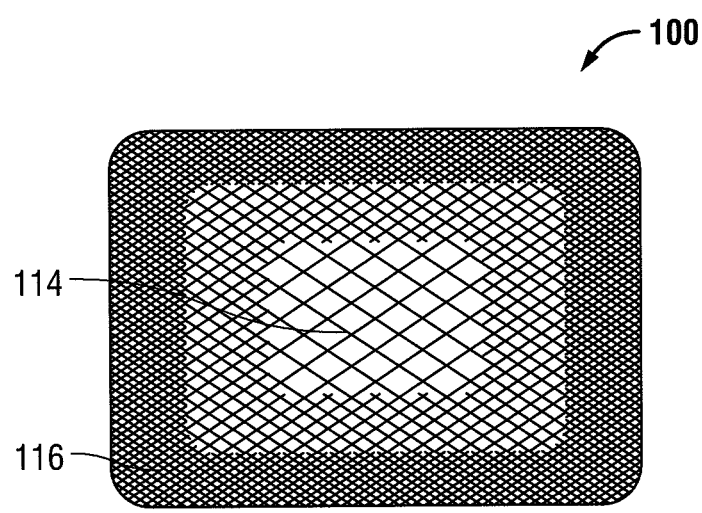
FIG. 10 schematically shows a medical device having a concentration gradient of a bioactive agent in accordance with an alternate embodiment of the present disclosure.

It should be understood that the gradient of bioactive agent used to coat the medical device according to the present disclosure may vary. For example, as illustrated in FIG. 10, the concentration gradient may increase from the peripheral portions 116 to the central portion 114 of the mesh. In one embodiment, the lower concentration of a first bioactive agent disposed in the central portion 114 may be more therapeutically effective compared to a higher concentration of a second bioactive agent disposed in the peripheral portions 116. In other embodiments, the peripheral portion may include a first bioactive agent, which is different from a second bioactive agent disposed in the central portion 114. The concentration gradient may also increase across the surface of the mesh from one side to another (e.g., left to right, top to bottom, corner to corner, etc.). Various concentrations of bioactive agents may be positioned along any portion of the mesh. Other variations are also within the purview of those skilled in the art.

It is envisioned that the medical devices described herein may further include a plurality of concentration gradients. In such embodiments, a single bioactive agent may be disposed on the medical device in a manner wherein the concentration of the agent increases and decreases more than once across the surface of the device. Alternatively, in some embodiments, a plurality of bioactive agents may be disposed across the implant wherein each bioactive agent represents a different concentration gradient. For example, a first bioactive agent may be disposed to create a continuous concentration gradient and a second bioactive agent may be disposed to create a discontinuous concentration gradient.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments of the present disclosure. Various modifications and variations of the medical device, bioactive agent concentration gradients, and coating methods and patterns will be apparent to those skilled in the art from the foregoing detailed description. Such modifications and variations are intended to come within the scope and spirit of the claims appended hereto.

What is claimed is:

1. A medical device comprising:
   a substrate including a plurality of fibers, the substrate defining a central portion and a peripheral portion;
   a first bioactive agent disposed within a continuous, single polymeric film or foam extending over at least a portion of an outer surface of at least two fibers of the plurality of fibers of the substrate, wherein a higher concentration of the first bioactive agent is on the central portion of the substrate and a lower concentration of the first bioactive agent extends outwardly from the central portion towards the peripheral portion of the substrate; and
   a second bioactive agent disposed within a plurality of polymeric capsules in a flowable state, the polymeric capsules positioned on an intermediate portion of the substrate between the central portion and the peripheral portion.

2. The medical device according to claim 1, wherein the first bioactive agent extends through the peripheral portion of the substrate.

3. The medical device according to claim 1, wherein the first bioactive agent is disposed on the substrate as a substantially continuous concentration gradient.

4. The medical device according to claim 1, wherein the first bioactive agent is disposed on the substrate as a discontinuous concentration gradient.

5. The medical device according to claim 1, wherein the substrate includes a concentration gradient of the first bioactive agent in a height dimension of the substrate.

6. The medical device according to claim 1, wherein the first bioactive agent is disposed within pores of the substrate thereby creating a concentration gradient in a height dimension of the substrate.

7. The medical device according to claim 1, further comprising markings on the substrate for visualization of the first bioactive agent.

8. The medical device according to claim 1, wherein the first bioactive agent is selected from the group consisting of anti-adhesives, antimicrobials, analgesics, antipyretics, anesthetics, anti-arrhythmic agents, anti-depressants, vasodilators, antiepileptics, antihistamines, anti-inflammatories, antipsychotics, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors, enzymes, and combinations thereof.

9. The medical device according to claim 1, wherein the first bioactive agent is selected from the group consisting of capsaicin, bupivacaine and bupivacaine hydrochloride.

10. The medical device according to claim 1, wherein the first bioactive agent is released from the substrate over a period of time ranging from about 1 second to about 21 days.

11. The medical device according to claim 1, wherein the first bioactive agent is released from the substrate over a period of time ranging from about 1 minute to about 14 days.

12. The medical device according to claim 1, further comprising at least one additional bioactive agent.

13. A medical device comprising:
   a substrate including a plurality of fibers, the substrate defining a central portion and a peripheral portion;
   a first bioactive agent disposed within a continuous, single polymeric film or foam extending over at least a portion of an outer surface of at least two fibers of the plurality of fibers of the substrate, wherein a lower concentration of the first bioactive agent is on the central portion of the substrate and a higher concentration of the first bioactive agent extends outwardly from the central portion towards the peripheral portion of the substrate; and
   a second bioactive agent disposed within a plurality of polymeric capsules in a flowable state, the polymeric capsules positioned on an intermediate portion of the substrate between the central portion and the peripheral portion.

14. The medical device according to claim 13, wherein the first bioactive agent is different from the second bioactive agent.

15. The medical device according to claim 13, wherein the lower concentration is more therapeutically effective compared to the higher concentration.

16. The medical device according to claim 13, wherein the first and second bioactive agent is selected from the group consisting of capsaicin, bupivacaine, and bupivacaine hydrochloride.

17. The medical device according to claim 1, wherein the first bioactive agent is different from the second bioactive agent.

18. The medical device of claim 1 wherein the first and second bioactive agent are selected from the group consisting of capsaicin, bupivacaine, and bupivacaine hydrochloride.

19. The medical device according to claim 1, wherein each polymeric capsule of the plurality of polymeric capsules extends over at least a portion of an outer surface of at least two fibers of the plurality of fibers of the substrate.

20. The medical device according to claim 13, wherein each polymeric capsule of the plurality of polymeric capsules extends over at least a portion of an outer surface of at least two fibers of the plurality of fibers of the substrate.

* * * * *